(12) United States Patent
Chen et al.

(10) Patent No.: US 11,143,640 B2
(45) Date of Patent: Oct. 12, 2021

(54) ROTATING BUFFER STATION FOR A CHIP

(71) Applicant: Chroma Ate Inc., Taoyuan (TW)

(72) Inventors: Yung-Chih Chen, Taoyuan (TW); Chien-Ming Chen, Taoyuan (TW); Yun-Jui Cheng, Taoyuan (TW)

(73) Assignee: CHROMA ATE INC., Taoyuan (TW)

( * ) Notice: Subject to any disclaimer, the term of this patent is extended or adjusted under 35 U.S.C. 154(b) by 266 days.

(21) Appl. No.: 16/540,162

(22) Filed: Aug. 14, 2019

(65) Prior Publication Data
US 2020/0057037 A1    Feb. 20, 2020

(30) Foreign Application Priority Data
Aug. 15, 2018  (TW) .................................. 107128419

(51) Int. Cl.
*G01N 33/00*  (2006.01)

(52) U.S. Cl.
CPC ..... *G01N 33/00* (2013.01); *G01N 2033/0095* (2013.01)

(58) Field of Classification Search
CPC ....................... G01N 33/00; G01N 2033/0095
See application file for complete search history.

(56) References Cited

U.S. PATENT DOCUMENTS

| | | | | |
|---|---|---|---|---|
| 4,313,266 A * | 2/1982 | Tam | ........................ | C30B 33/00 34/317 |
| 5,117,590 A * | 6/1992 | Kudo | ...................... | B24B 9/065 451/239 |
| 6,093,930 A * | 7/2000 | Boyette, Jr. | ............ | G01Q 70/02 250/442.11 |
| 6,156,124 A * | 12/2000 | Tobin | .................... | B24B 37/345 118/500 |
| 6,249,342 B1 * | 6/2001 | Cheng | ................ | G01R 31/2887 356/237.2 |
| 7,649,157 B2 * | 1/2010 | Iizuka | ................ | B23K 26/0884 219/121.82 |
| 2009/0061739 A1 * | 3/2009 | Jeong | .................... | B24B 37/345 451/41 |

* cited by examiner

*Primary Examiner* — Nathaniel T Woodward
(74) *Attorney, Agent, or Firm* — McClure, Qualey & Rodack, LLP

(57) ABSTRACT

A rotating buffer station for a chip mainly comprises an upper cover plate, a rotatable plate, a movable jaw member and a lower base. The upper cover plate is arranged on the lower base and formed with a guide slot. The rotatable plate is located between the lower base and the upper cover plate and formed with a cam slot. The rotatable plate is pivotally coupled to the lower base. The movable jaw member is slidably engaged with the cam slot and the guide slot. When the rotatable plate is rotated, the cam slot forces the movable jaw member to move radially along the guide slot so as to form a chip socket. Accordingly, with rotation of the rotatable plate, the cam slot forces the movable jaw member to move radially along the guide slot so that the chip socket can be resized to hold various differently-sized chips.

10 Claims, 4 Drawing Sheets

ROTATING BUFFER STATION FOR A CHIP

FIELD OF THE INVENTION

The present invention relates to a rotating buffer station for a chip and more particularly to a rotating buffer station for a chip suitable for use in a chip inspection apparatus or a chip manufacturing apparatus.

DESCRIPTION OF THE PRIOR ART

During fabrication or inspection of chips, it may be necessary to place a chip in a specific orientation or rotate the chip by a specific angle. For example, if the orientation of the chip placed in a tray does not conform to the orientation in which the chip has to be placed in the chip test socket, positions of contacts of the chip picked from the tray would not correspond to probes in the chip test socket. As a result, the chip to be tested has to be placed on a rotating station, rotated by a specific angle by means of the rotating station and then transferred to and placed in the chip test socket.

FIG. 1 is a schematic perspective view of a conventional rotating station. As shown in FIG. 1, a chip socket 11 having four corners is disposed at the center of the rotating station 1, and each corner of the chip socket 11 communicated with a slot 12. A laser alignment device 13 is disposed at one end of the slot 12. The laser alignment device 13 is not only used for detecting presence of a chip to be tested in the chip socket 11 but also for determining whether the orientation of the chip to be tested is correct or not.

However, the size of the chip socket 11 of the conventional rotating station 1 is unchangeable. If the chip to be tested is changed to a differently-sized chip, the entire jig has to be replaced as the chip socket 11 is not suitable for differently-sized chips. That would be unfavorable for the process or shifting of differently-sized chips.

In view of the above, there is a demand for a rotating buffer station for a chip which is suitable for various differently-sized chips and which has a simple structure, is low-cost and has no need of an alignment device.

SUMMARY OF THE INVENTION

The object of the present invention is to provide a rotating buffer station for a chip which is capable of resizing a chip socket for holding the chip to be tested according to the size of the chip to be tested and which has a simple structure and is convenient for operation.

In order to achieve the above object, a rotating buffer station for a chip mainly comprises an upper cover plate, a rotatable plate, at least one movable jaw member and a lower base, wherein the upper cover plate is arranged on the lower base and formed with at least one guide slot, the rotatable plate is located between the lower base and the upper cover and formed with at least one cam slot, the rotatable plate is pivotally coupled to at least one of the lower base and upper cover plate, the at least one movable jaw member is slidably engaged with the at least one cam slot of the rotatable plate and the at least one guide slot of the upper cover plate, and wherein when the rotatable plate is rotated, the at least one cam slot forces the at least one movable jaw member to move radially along the at least one guide slot so as to form a chip socket for holding the chip.

As such, in the rotating buffer station of the present invention, the cam slot forces the movable jaw member to move radially along the guide slot so as to form a chip socket capable of holding various differently-sized chips. The chip socket of the present invention can be easily resized to hold differently-sized chips by rotating the rotatable plate.

Preferably, the upper cover plate of the rotating buffer station of the present invention may be disk-shaped, and the at least one guide slot is radially formed on the upper cover plate with respect to a center of the upper cover plate. Similarly, the rotatable plate of the present invention may be disk-shaped. The at least one cam slot is spirally formed on the rotatable plate with respect to a center of the rotatable plate.

The rotating buffer station of the present invention may further comprise a locking member. The upper cover plate may comprise a through hole. The rotatable plate may further comprise an outer annular slot. The lower base may comprise a locking hole. The locking member extends through the through hole and the outer annular slot and is screwed into the locking hole. In the case that the chip socket for the chip to be tested has been properly resized, the rotatable plate may be fixed by the locking member so as to prevent the rotatable plate from being rotated, thereby keeping the chip socket at a prescribed size.

Each movable jaw member of the rotating buffer station of the present invention may comprise a chip holding portion, a sliding key and a follower pin. The chip holding portion may be protruded from an upper surface of the upper cover plate. The sliding key is slidably engaged with the at least one guide slot of the upper cover plate while the follower pin is slidably engaged with the at least one cam slot of the rotatable plate. The chip holding portion is used to form a chip socket for holding the chip to be tested, the sliding key is freely slidable in the guide slot, and the follower pin is freely slidable in the cam slot.

The rotating buffer station of the present invention may further comprise a driving member which may be arranged in the lower base, and the driving member is coupled to the rotatable plate and arranged to rotate the rotatable plate. According to the present invention, the rotatable plate can be rotated by the driving member which may be a manually-operated device or an electrically-powered device such as an electric motor. The driving member may include a driving wheel. The lower base may comprise a circumferential wall. The circumferential wall comprises an axial notch, and the upper cover comprises a radial notch. The driving wheel is pivotally disposed in the axial notch and aligned with the radial notch. An outer circumferential surface of the driving wheel is in friction contact with a peripheral surface of the rotatable plate.

The rotating buffer station of the present invention may further comprise a turning base. The lower base may be mounted on the turning base. Accordingly, the orientation of the chip placed in the chip socket can be changed by the turning base. The turning base may comprise an electric motor for rotating the turning base.

An upper surface of the upper cover plate of the rotating buffer station of the present invention may be provided with a stationary jaw member. When the rotatable plate is rotated, the cam slot forces the movable jaw member to move toward or away from the stationary jaw member along the at least one guide slot. As such, the chip socket can be resized by movement of the movable jaw member with respect to the stationary jaw member.

Preferably, the rotating buffer station of the present invention may comprise four movable jaw members. The upper cover plate may be formed with four guide slots in a cross pattern. The rotatable plate may be equiangularly formed with four cam slots. The four movable jaw members are slidably engaged with the four cam slots of the rotatable plate, respectively and are slidably engaged with the four guide slots of the upper cover plate, respectively. By means of the four guide slots formed in a cross pattern, the chip socket can be resized by moving the four movable jaw members toward or away from each other.

DETAILED DESCRIPTION OF THE INVENTION

Figure 1:
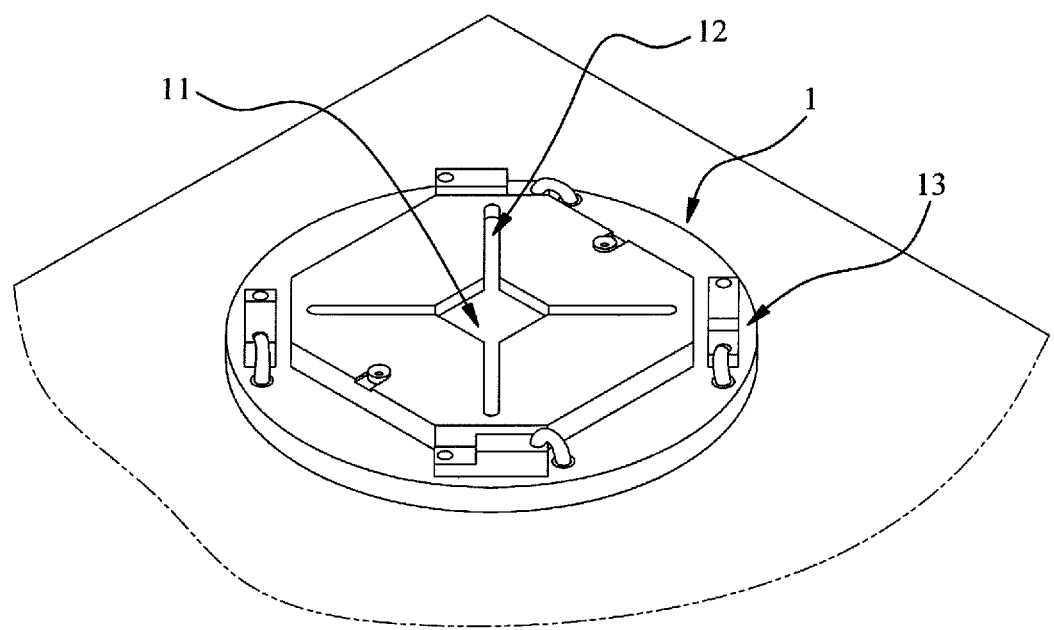
FIG. 1 is a schematic perspective view of a conventional rotating station.

In describing preferred embodiments of a rotating buffer station for a chip of the present invention in detail, it is noted that similar elements are designated by the same reference numerals. The drawings of the present invention are merely illustrative and are not necessarily drawn to scale, and all details are not necessarily shown in the drawings.

Figure 2:
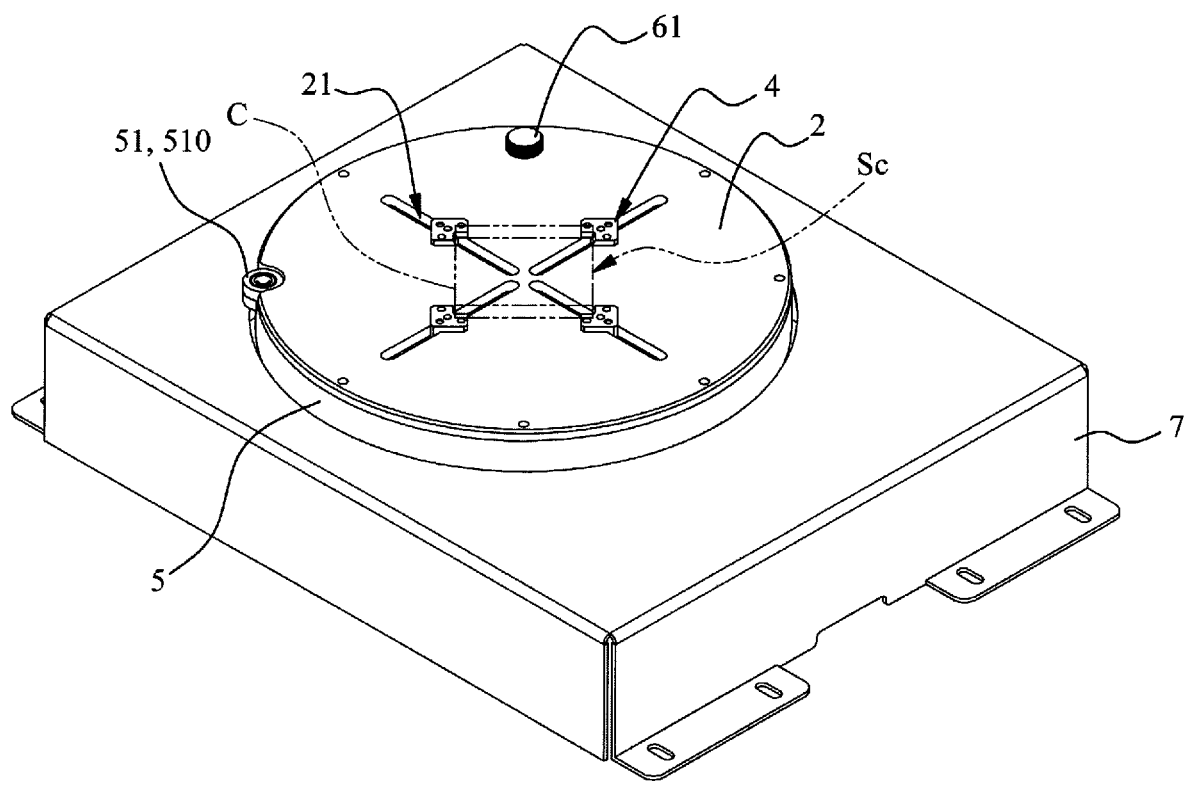
FIG. 2 is a perspective view of the first embodiment of the present invention.
Figure 3:
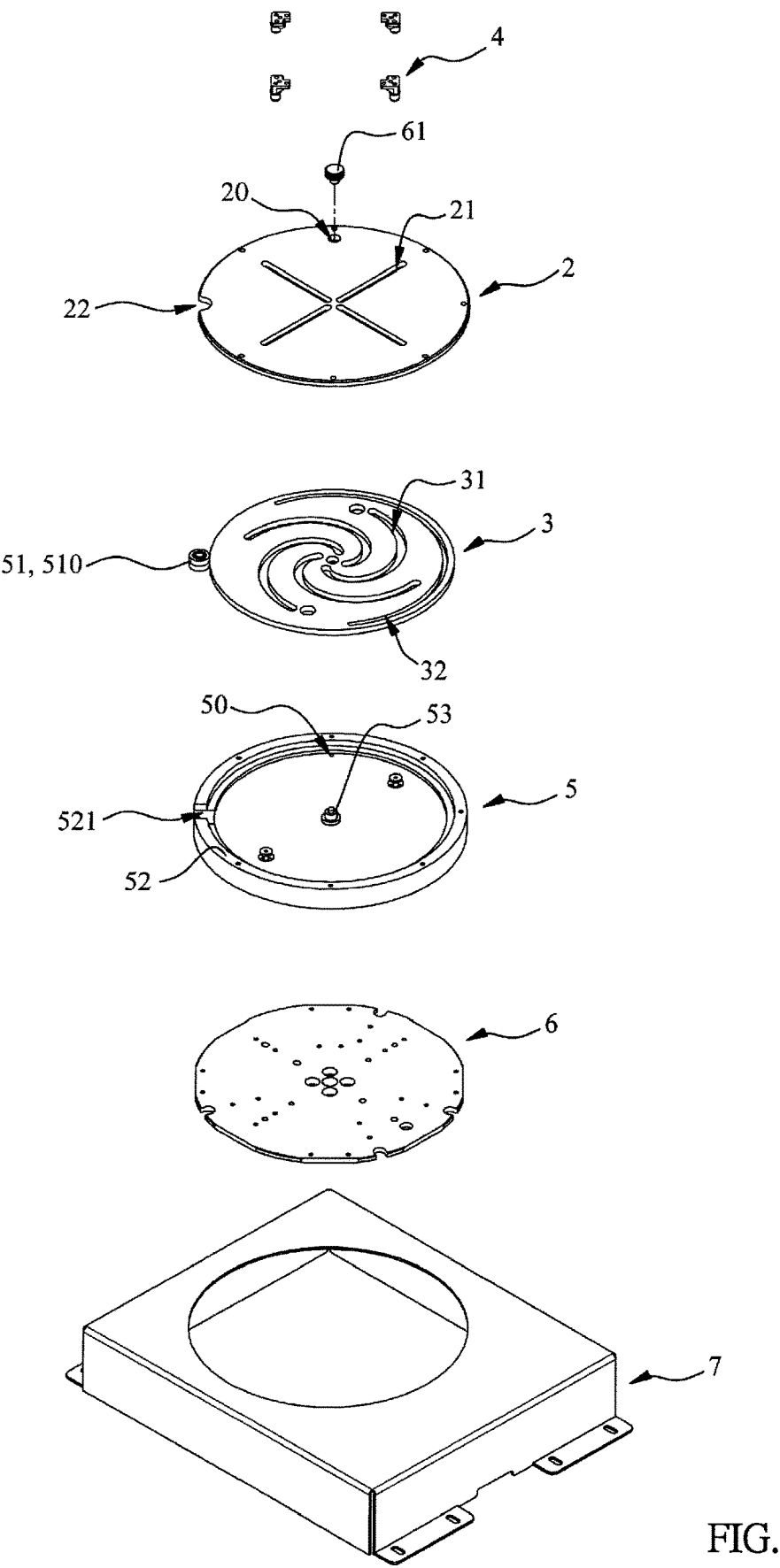
FIG. 3 is an exploded view of the first embodiment of the present invention.
Figure 4:
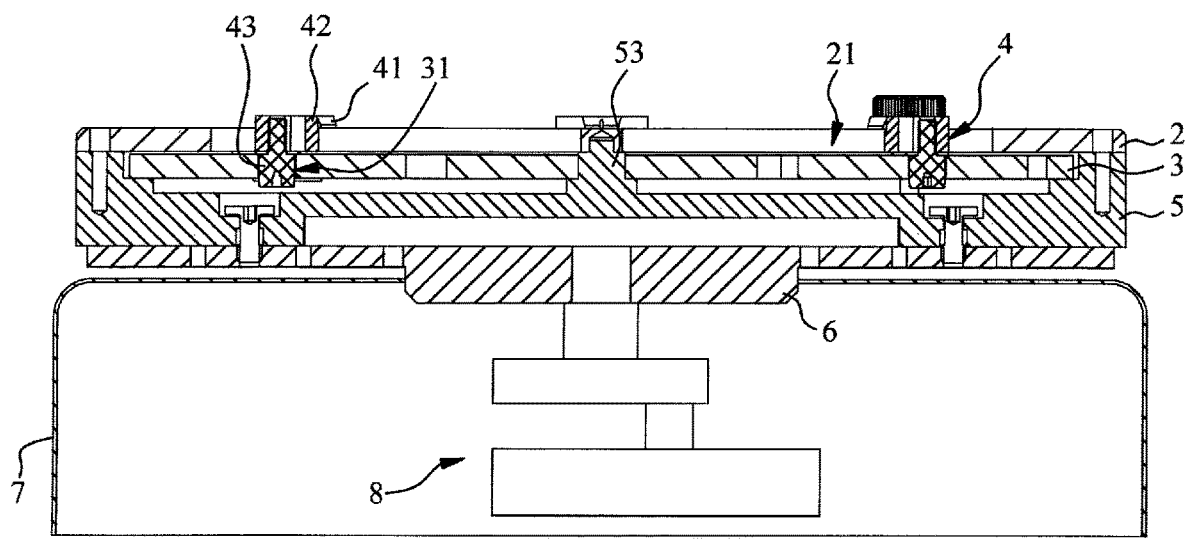
FIG. 4 is a cross-sectional view of the first embodiment of the present invention.

In describing the first embodiment of the present invention, reference is made to FIG. 2, FIG. 3 and FIG. 4. FIG. 2 is a perspective view of the first embodiment of the present invention. FIG. 3 is an exploded view of the first embodiment of the present invention. FIG. 4 is a cross-sectional view of the first embodiment of the present invention. As shown in the figures, the rotating buffer station of the first embodiment mainly comprises an upper cover plate 2, a rotatable plate 3, four movable jaw members 4, a lower base 5, a turning base 6 and a housing 7.

The upper cover plate 2 of the first embodiment is disk-shaped and is formed with four guide slots 21. The four guide slots 21 are radially and equiangularly formed with respect to the center of the upper cover plate 2. That is, the four guide slots 21 are formed in a cross pattern. The rotatable plate 3 of the first embodiment is also disk-shaped and is formed with four cam slots 31 which are equiangularly and spirally formed with respect to the center of the rotatable plate 3.

Figure 5:
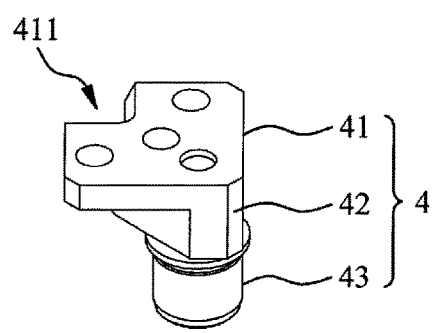
FIG. 5 is a perspective view of a movable jaw member according to the first embodiment of the present invention.

Reference is made to FIG. 5. FIG. 5 is a perspective view of the movable jaw member of the first embodiment of the present invention. Each movable jaw member 4 of the first embodiment comprises a chip holding portion 41, a sliding key 42 and a follower pin 43. The chip holding portion 41 is provided with a right-angle cutout portion 411 corresponding to one of four corners of the chip C to be tested (as shown in FIG. 2). The right-angle cutout portions 411 of the four movable jaw members 4 respectively correspond to the four corners of the chip C to be tested and form a chip socket Sc for accommodating the chip C to be tested.

As shown in FIG. 4, the movable jaw member 4 is slidably engaged with the cam slot 31 of the rotatable plate 3 and the guide slot 21 of the upper cover plate 2. Specifically, the sliding key 42 of the movable jaw member 4 is slidably engaged with the guide slot 21 of the upper cover plate 2 while the follower pin 43 is slidably engaged with the cam slot 31 of the rotatable plate 3. The chip holding portion 41 is protruded from the upper surface of the upper cover plate 2.

Reference is made to FIG. 3 and FIG. 4. The upper cover plate 2 is mounted on the lower base 5 such that the rotary plate 3 is located between the lower base 5 and the upper cover plate 2. The rotary plate 3 is pivotally coupled to a central pin 53 of the lower base 5 such that the rotatable plate 3 is freely rotatable with respect to the upper cover plate 2 and the lower base 5. The lower base 5 comprises a circumferential wall 52 which is formed with an axial notch 521. The upper cover plate 2 is formed with a radial notch 22. In the first embodiment, a driving member 51 is disposed in the axial notch 521 of the lower base 5 and aligned with the radial notch 22, and an outer circumferential surface of the driving wheel 510 is in friction contact with a peripheral surface of the rotatable plate 3.

Furthermore, the first embodiment further comprises a locking member 61. The upper cover plate 2 is formed with a through hole 20. The rotatable plate 3 further comprises an outer annular slot 32. The lower base 5 is formed with a locking hole 50. The locking member 61 extends through the through hole 20 and the outer annular slot 32 and is screwed into the locking hole 50.

Figure 6:
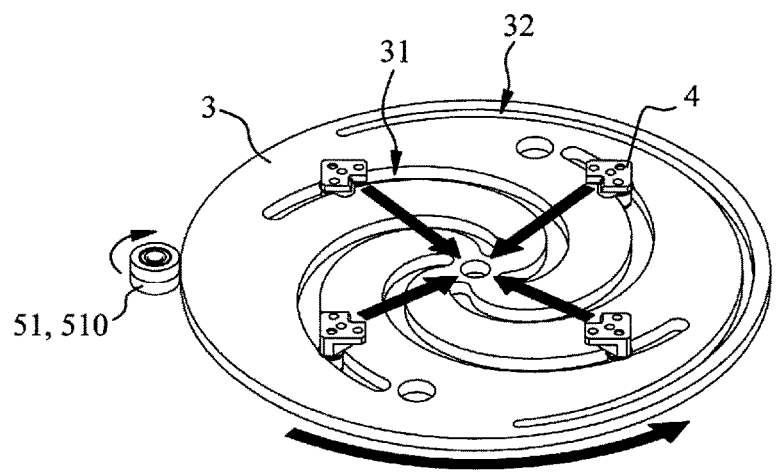
FIG. 6 is a view showing that rotation of the rotary plate of the first embodiment of the present invention causes the movable jaw members to move inwardly.

In the following description, the operation of resizing the chip socket Sc of the first embodiment will be described. Reference is made to FIG. 6. FIG. 6 is a schematic view showing that rotation of the rotatable plate of the first embodiment of the present invention in one direction causes the movable jaw members to move inwardly. In the case that the chip socket Sc has to be resized to conform with a differently-sized chip to be tested, the driving wheel 510 is manually rotated so as to rotate the rotatable plate 3. Of course, in other embodiments of the present invention, the drive wheel 510 may be rotated by an electric motor.

With rotation of the rotatable plate 3, the four cam slots 31 which are formed spirally force the four movable jaw members 4 to move toward or away from each other synchronously and radially along the guide slots 21. If resizing of the chip socket is completed, the locking member 61 can be used to manually lock the rotatable plate 3, thereby keeping the chip socket Sc at a prescribed size and avoiding unintentional rotation of the rotatable plate 3 or unintentional movement of the movable jaw members 4.

Reference is made to FIG. 3 and FIG. 4. The first embodiment further comprises a turning base 6 pivotally coupled to the housing 7. The lower base 5 is mounted on the turning base 6. The turning base 6 is further connected with a rotating drive module 8, which may be composed of a motor and a speed reduction mechanism. The rotating drive module 8 is capable of rotating the turning base 6 and hence rotating the assembly of the upper cover plate 2, the rotatable plate 3, the chip socket Sc formed by the four movable jaw members 4 and the lower base 5. The chip socket Sc and the chip C to be tested accommodated therein can be rotated by a specific angle, for example, 90 degrees or 180 degrees.

Figure 7A:
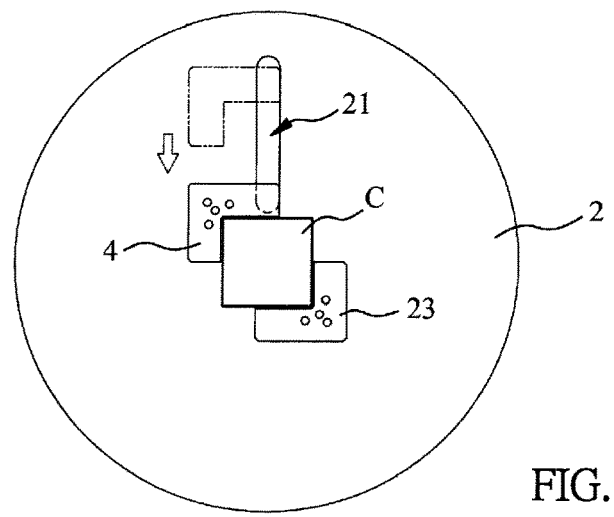
FIG. 7A is a schematic view of the second embodiment of the present invention.

Reference is made to FIG. 7A. FIG. 7A schematically shows a second embodiment of the present invention. The second embodiment of the present invention comprises a single movable jaw member 4. The upper surface of the upper cover plate 2 is provided with a stationary jaw member and is formed with one guide slot 21, and the rotatable plate is formed with one cam slot (not shown). When the rotatable plate is rotated, the cam slot forces the movable jaw member 4 to move toward or away from the stationary jaw member 23 along the guide slot 21, thereby resizing the chip socket.

Figure 7B:
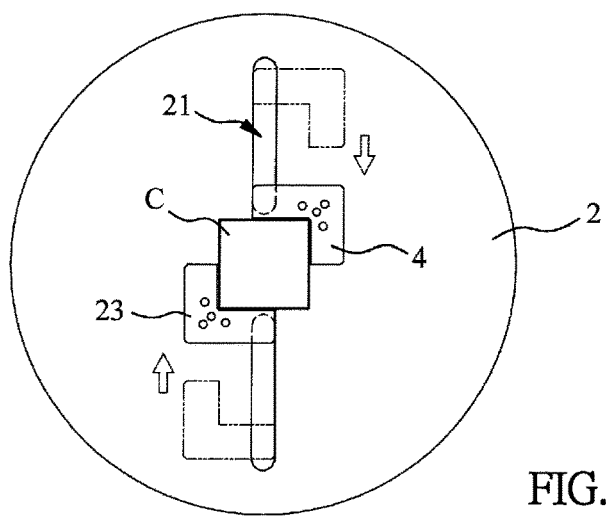
FIG. 7B is a schematic view of the third embodiment of the present invention.

Reference is made to FIG. 7B. FIG. 7B schematically shows a third embodiment of the present invention. As shown in FIG. 7B, the third embodiment of the present invention comprises two movable jaw members 4. The upper cover plate 2 is formed with two guide slots 21, and the rotatable plate is formed with two cams slots (not shown). When the rotatable plate is rotated, the two cam slots force the two movable jaw member 4 to move toward or away from each other along the two guide slots 21, thereby resizing the chip socket.

Figure 7C:
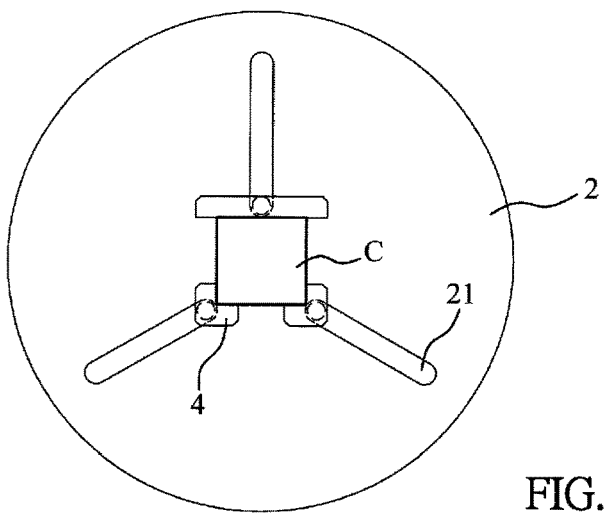
FIG. 7C is a schematic view of the fourth embodiment of the present invention.

Reference is made to FIG. 7C. FIG. 7C schematically shows a fourth embodiment of the present invention. As shown in FIG. 7C, the fourth embodiment of the present invention comprises three movable jaw members 4. The upper cover plate 2 is formed with three guide slots 21, and the rotatable plate is formed with three cam slots (not shown). When the rotatable plate is rotated, the three cam slots force the three movable jaw members 4 to move toward or away from each other along the three guide slots 21, thereby resizing the chip socket.

In summary, the amount and shape of the movable jaw member 4 can be selected according to the sizes or shapes of chips to be tested, such as square ICs, circular ICs or rectangular ICs. The rotating buffer station of the present invention can be further equipped with an automatic optical inspection device (AO') and a laser alignment device for alignment and calibration of the chips to be tested.

It should be understood that the embodiments and the accompanying drawings have been described for illustrative purposes and are not limiting. Accordingly, it is intended that the invention not be limited to the disclosed embodiments, but that it have the full scope permitted by the language of the following claims.

What is claimed is:

1. A rotating buffer station for a chip comprising:
    a lower base;
    an upper cover plate formed with at least one guide slot, the upper cover plate being disposed on the lower base;
    a rotatable plate formed with at least one cam slot, the rotatable plate being located between the lower base and the upper cover plate and pivotally coupled to at least one of the lower base and the upper cover plate; and
    at least one movable jaw member slidably engaged with the at least one cam slot of the rotatable plate and the at least one guide slot of the upper cover plate;
    wherein the rotating buffer station is configured such that when the rotatable plate is rotated, the at least one cam slot forces the at least one movable jaw member to move radially along the at least one guide slot so as to form a chip socket.

2. The rotating buffer station of claim 1, wherein the upper cover plate is disk-shaped, and the at least one guide slot is radially formed on the upper cover plate with respect to a center of the upper cover plate.

3. The rotating buffer station of claim 1, wherein the rotatable plate is disk-shaped, and the at least one cam slot is spirally formed on the rotatable plate with respect to a center of the rotatable plate.

4. The rotating buffer station of claim 3 further comprising a locking member,
    wherein the upper cover plate comprises a through hole, the rotatable plate comprises an outer annular slot, the lower base plate comprises a locking hole; and
    the locking member extends through the through hole and the outer annular slot and is screwed into the locking hole.

5. The rotating buffer station of claim 1, wherein each movable jaw member comprises a chip holding portion, a sliding key and a follower pin, the chip holding portion is protruded from an upper surface of the upper cover plate, the sliding key is slidably engaged with the at least one guide slot of the upper cover plate, and the follower pin is slidably engaged with the at least one cam slot of the rotatable plate.

6. The rotating buffer station of claim 1 further comprising a driving member arranged in the lower base, wherein the driving member is coupled to the rotatable plate and provided to rotate the rotatable plate.

7. The rotating buffer station of claim 6, wherein the driving member comprises a driving wheel, the lower base comprises a circumferential wall, the circumferential wall comprises an axial notch, the upper cover plate comprises a radial notch; and
    the drive wheel is pivotally disposed in the axial notch and aligned with the radial notch, and an outer circumferential surface of the drive wheel is in friction contact with a peripheral surface of the rotatable plate.

8. The rotating buffer station of claim 1 further comprising a turning base on which the lower base is mounted.

9. The rotating buffer station of claim 1, wherein an upper surface of the upper cover plate is provided with a stationary jaw member,
    configured such that when the rotatable plate is rotated, the at least one cam slot forces the at least one movable jaw member to move toward or away from the stationary jaw member along the at least one guide slot.

10. The rotating buffer station of claim 1 comprising four movable jaw members,
    wherein the upper cover plate is formed with four guide slots in a cross pattern;
    the rotatable plate is formed with four cam slots equiangularly;
    the four movable jaw members are slidably engaged with the four cam slots of the rotatable plate, respectively and are slidably engaged with the four guide slots of the upper cover plate, respectively.

* * * * *